(12) United States Patent
Chuah et al.

(10) Patent No.: US 7,329,403 B2
(45) Date of Patent: Feb. 12, 2008

(54) COSMETIC COMPOSITIONS

(75) Inventors: Beng Sim Chuah, Selangor (MY);
Bruce Steven Emslie, Wiral (GB);
Kevin Ronald Franklin, Wirral (GB);
Daniel Albert Martindale, Wirral (GB); Graham Andrew Turner, Wirral (GB)

(73) Assignee: Unilever Home & Personal Care USA Division of Conopco, Inc., Chicago, IL (US)

( * ) Notice: Subject to any disclaimer, the term of this patent is extended or adjusted under 35 U.S.C. 154(b) by 144 days.

(21) Appl. No.: 10/603,318

(22) Filed: Jun. 25, 2003

(65) Prior Publication Data
US 2005/0002883 A1 Jan. 6, 2005

(30) Foreign Application Priority Data
Jun. 26, 2002 (GB) .................................. 0214805.4

(51) Int. Cl.
*A61K 8/46* (2006.01)
(52) U.S. Cl. ....................................................... 424/65
(58) Field of Classification Search ................ 424/489, 424/65
See application file for complete search history.

(56) References Cited

U.S. PATENT DOCUMENTS

| 5,221,534 | A | * | 6/1993 | DesLauriers et al. | .... 424/78.03 |
| 5,750,096 | A | * | 5/1998 | Guskey | ........................ 424/65 |
| 6,143,284 | A | | 11/2000 | Bush et al. | ................... 424/65 |
| 6,403,070 | B1 | * | 6/2002 | Pataut et al. | .................. 424/65 |
| 6,485,716 | B1 | * | 11/2002 | Fei et al. | ....................... 424/65 |
| 6,986,885 | B2 | * | 1/2006 | Mattai et al. | ................. 424/65 |

* cited by examiner

*Primary Examiner*—Michael Woodward
*Assistant Examiner*—Bethany Barham
(74) *Attorney, Agent, or Firm*—Karen E. Klumas

(57) ABSTRACT

Cosmetic compositions in the form of soft solids having in combination an improved resistance to syneresis and retained efficacy and which contain a particulate antiperspirant suspended in a water-immiscible carrier liquid structured by a structurant system are obtainable by employing as carrier liquid a mixture of a hydrocarbon oil and an aromatic ester oil in a weight ratio of from 1:2 to 15:1 and as structurant system from 5.5 to 20% in total of a di or triblock alkylene/arylene block copolymer and an organic wax in a weight ratio to each other of from 5:1 to 30:1.

34 Claims, 1 Drawing Sheet

Figure 1

US 7,329,403 B2

COSMETIC COMPOSITIONS

The present invention relates to cosmetic compositions, especially compositions intended for topical application to the body containing an antiperspirant and particularly to compositions in the form of soft solids.

BACKGROUND AND PRIOR ART

Cosmetic compositions containing an antiperspirant that are intended for topical application to the body are available to the public in a number of product forms, of which one form that has been popular in the last 10 years is that of soft solids. These have sometimes alternatively been referred to as semi-solids or as anhydrous creams. In essence, and irrespective of the name used, the soft solid comprises a particulate antiperspirant active that is dispersed within a water-immiscible carrier fluid that is structured by one or more structurants. It is commonly stored in a dispensing container which comprises a product chamber, usually a round or oval cylinder, having at one end a cover defining a number of apertures through which the contents of the chamber can be dispensed and a means to expel the contents through the apertures. That means can comprise squeezable side-walls, or more commonly a platform or elevator at an intermediate position within the cylindrical chamber that can be advanced towards the first end.

In order for the soft solid to be dispensed through the aperture(s) in the cover of the chamber, the rheological properties of the composition are altered when it is subjected to mild pressure and especially in the vicinity of the aperture wall compared with the normal state that existed prior to the soft solid being extruded under pressure through those apertures. When pressurised and extruded through the aperture, the micro-structure of the solidified carrier liquid is partly destroyed adjacent to its contact boundary with the aperture, so that the viscosity of the composition is locally reduced, thereby enabling the composition to flow. This subsequently becomes especially noticeable in the vicinity of the apertures through which the composition is being dispensed. The micro-structure of the composition that has been extruded through the apertures or that which remains within or close to the apertures may often not reform to a significant extent or at best reform only extremely slowly when the pressure on the composition is released, with the result that after the composition has been subjected to pressure and partial extrusion, it still has a lower viscosity in the vicinity of the cover apertures. Indeed, a separate localised liquid phase can be formed, particularly from one or more of the oils in which particulate materials are suspended. An undesired consequence of the formation of a separate liquid phase is a problem called syneresis, in which the liquid phase, particularly the oils, can seep out of the chamber, or possibly be expelled from the chamber as a consequence of residual or subsequent pressure in the container, onto the surface of the dispensing container, and possibly trickling down the sides of the container.

Although damage to the microstructure of the soft solid occurs at the time of extrusion through the cover apertures, the appearance of the oils or other liquid on the surface tends to be retarded, because it takes a finite period of time for transfer of fluid from within the container. Thus, the extent of liquid on the container surface tends to increase for a period of maybe half an hour to 2 or 3 hours after the product has been dispensed (and applied topically to the armpit) depending on the oils and the structurants employed. Thereafter, there tends to be little, if any, additional egress of oil. However, once the oil has egressed, there is no mechanism for its subsequent recapture by the remaining composition within the container. Moreover, since the problem of syneresis does not occur instantly, but develops during the period of at least half an hour later, the consumer normally does not have an opportunity to take remedial action by wiping the container after the oils have appeared. If wiping were done shortly after use, the problem would materialise subsequently. Consequently, whether on the top or sides, the oils can form a sticky and often unsightly mess, possibly after partial evaporation. This is not liked by consumers who wish to use dispensers that are not sticky to hold or unsightly to view.

Consequently, in one respect, the problem that the instant invention seeks to address is how to formulate a soft solid composition so that the problem of syneresis is eliminated or at least ameliorated.

One strategy that has been proposed by some patentees to combat the problem of syneresis comprises incorporating a pressure-relief mechanism that forms part of or is linked to the mechanism that expels soft solid out of the dispenser comprises means to reduce the extent of pressure generation in the dispenser for soft solids.

These mechanisms can include suck-back mechanisms to automatically partially withdraw the elevator or platform away from the cover immediately subsequent to its advancement, thereby increasing the volume available for the soft solid within the dispenser between the platform and top wall and accordingly reducing the pressure immediately. A second means which mitigates the problem by increasing the ratio of the volume of composition that is extruded relative to the aperture sidewall length comprises increasing the proportion of apertures in the top wall. The two means may be employed together. (U.S. Pat. No. 6,143,284). However, a pressure release mechanism mentioned above can render more complicated the advance mechanism, and increase the cost of the dispenser, which already can constitute a very significant proportion of the total cost of the product. Furthermore, it does not address the fundamental question of how to reduce the inherent susceptibility of the composition to syneresis.

The problem of its syneresis is not the only problem that is potentially associated with a soft solid composition.

In the course of investigating the suitability of a number of antiperspirant compositions to carry out their intended purpose, the instant inventors have recognised that changes to the constitution of the carrier liquid and structurants can not only alter the susceptibility or resistance of the composition to syneresis, but can simultaneously impair the inherent capability of the suspended antiperspirant to control perspiration when the composition has been applied topically onto human skin, such as in axilary regions. Moreover, any resultant composition still needs to be capable of being dispensed through the top wall of the dispenser when subjected to mild pressure. Accordingly, the problem faced by the instant inventors was to devise soft solid compositions that not only enjoyed an improved inherent resistance to syneresis, whilst simultaneously remaining dispensable, but at the same time also maintaining an acceptable capability to control perspiration.

SUMMARY OF THE INVENTION

According to a first aspect of the present invention, there is provided a cosmetic composition comprising;
  at least 60% by weight in total of a water immiscible carrier liquid and structurant system therefor, and from 1 to 30% by weight of a particulate antiperspirant active suspended in said carrier liquid said carrier liquid comprising a mixture of a hydrocarbon oil and an aromatic ester oil in a weight ratio of from 1:2 to 15:1 and said structurant system comprising from 5.5 to 20% in total of a di or triblock alkylene/arylene block copolymer and an organic wax in a weight ratio to each other of from 5:1 to 30:1.

The present invention is founded upon the provision simultaneously of not only a carrier liquid which is a mixture of two essential components, namely the hydrocarbon oil and the aromatic ester oil but also a combination of the organic wax and the hydrocarbon block copolymer. By so selecting the carrier oil mixture and the combination of structurants specified above, it is possible to create an anhydrous antiperspirant composition that displays an enhanced resistance to syneresis even through dispensers which do not contain means to limit syneresis and which maintains an acceptable capability to control perspiration. The invention compositions can also exhibit further beneficial properties, such as desirable sensory properties, reducing or eliminating visible deposits on the skin or being translucent, depending upon the choice of the individual constituents and their proportions.

According to a second aspect of the present invention there is provided a cosmetic product comprising an anhydrous soft solid cosmetic composition contained within a dispensing container comprising a chamber for the cosmetic composition provided at one end with a closure defining at least one aperture and with a means for impelling the cosmetic composition towards the closure, in which the cosmetic composition is in accordance with the first aspect of the present invention. Suitably, the dispensing container is free from immediate pressure reducing means.

According to a third aspect there is provided a process of making a cosmetic product comprising a dispensing container comprising a chamber for a cosmetic composition provided at one end with a closure defining at least one aperture and with a means for impelling the antiperspirant composition towards the closure, wherein the cosmetic composition is in accordance with the first aspect, and the process comprises the steps of i) forming a mixture of the organic wax and at least a fraction or component of the carrier fluid mixture comprising hydrocarbon oil and/or aromatic ester oil;
ii) stirring the mixture and raising its temperature to a temperature selected within the range of from 50 to 120° C. at which the mixture is homogeneous;
iii) introducing into the mixture the copolymer, optionally premixed with the remainder of the carrier liquid, stirring the augmented mixture and maintaining or elevating its temperature within the range of up to 120° C. until it is homogeneous;
iv) introducing the particulate antiperspirant with stirring into the homogenous augmented mixture at a temperature above its normal setting temperature;
v) introducing the resultant antiperspirant-containing mixture into the chamber of the dispenser and
vi) cooling the antiperspirant-containing composition or allowing it to cool to below a temperature at which it forms a soft solid.

DETAILED DESCRIPTION OF THE INVENTION AND PREFERRED EMBODIMENTS

The present invention relates to a cosmetic composition containing a particulate antiperspirant active, a combination of selected oils in desired proportions forming a water-immiscible carrier liquid that is structured by a combination of a specified block copolymer and an organic wax. Herein such a composition can be referred to as an antiperspirant composition. The individual constituents of the composition and preferred embodiments of the invention will now described in greater detail, as well as a number of optional constituents, the incorporation of each of which can result in desirable or preferred compositions.

Antiperspirant Actives

The composition preferably contains an antiperspirant active. Antiperspirant actives, are preferably incorporated in an amount of from 0.5-60%, particularly from 5 to 30% or 40% and especially from 5 or 10% to 30 or 35% of the weight of the composition.

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates and activated aluminium chlorohydrates.

Aluminium halohydrates are usually defined by the general formula $Al_2(OH)_xQ_y.wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever N V et al), the contents of which specification is incorporated herein by reference. Some activated salts do not retain their enhanced activity in the presence of water but are useful in substantially anhydrous formulations, i.e. formulations which do not contain a distinct aqueous phase.

Zirconium actives can usually be represented by the empirical general formula: $ZrO(OH)^{2n-nz}B^z.wH_2O$ in which z is a variable in the range of from 0.9 to 2.0 so that the value 2n–nz is zero or positive, n is the valency of B, and B is selected from the group consisting of chloride, other halide, sulphamate, sulphate and mixtures thereof.

Possible hydration to a variable extent is represented by $wH_2O$. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have coordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_2(NH_2)COOH$.

It is highly desirable to employ complexes of a combination of aluminium halohydrates and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis.

Other actives which may be utilised include astringent titanium salts, for example those described in GB 2299506A.

The proportion of solid particulate antiperspirant salt in a suspension composition normally includes the weight of any water of hydration and any complexing agent that may also be present in the solid active.

The antiperspirant active may comprise such salts or mixture of such salts by themselves, but may alternative comprise a combination of such salts with a water-soluble polymer comprising Brønsted acid groups that acts as a co-gellant for the antiperspirant salt when mixed therewith in the presence of water, preferably in a weight ratio of the salt to the polymer of from 25:1 to 1:10. Preferably, the polymer is an organic polymer possessing a carbon backbone, optionally interrupted by ester or amide groups and having less than 50 mole % of positively-charged monomer units. The polymer very desirably comprises carboxylic acid groups or precursor thereof, and particularly has an acid value of greater than 160, for example being derivable from maleic acid or anhydride monomer. If employed, the polymer is normally present in discrete particles.

The composition takes the form of a suspension in which antiperspirant active in particulate form is suspended in the water-immiscible liquid carrier. Antiperspirant composition according to the present invention do not have any separate aqueous phase present and may conveniently be referred to as "anhydrous" although it should be understood that some water may be present bound to the antiperspirant active or as a small amount of solute within the water-immiscible liquid phase. In such compositions, the particle size of the antiperspirant salts often falls within the range of 0.1 to 200 μm with a mean particle size often from 3 to 30 μm. Actives having either larger or smaller mean particle sizes can also be contemplated such as from 30 to 50 μm or 0.1 to 3 μm.

The particulate antiperspirant active may be present in the form of hollow spheres or dense particles (by which is meant particles which are not hollow) at the discretion of the manufacturer. Where it is desired that the composition is translucent in bulk or to reduce the appearance of visible deposits on the skin to which the composition is applied or on clothing which comes into contact with the composition, it is preferable for the particles to be substantially free from hollows. As has previously been described, hollows can be eliminated by crushing the spheres. Furthermore for translucent bulk compositions, it is highly desirable to employ actives having no greater than a minor weight proportion of particles of below 10 μm diameter, for example by selecting an active having a mean particle size of from 12 to 30 μm diameter.

Carrier Liquid

The water-immiscible carrier liquid herein comprises a mixture of materials which are relatively hydrophobic so as to be immiscible in water. The invention employs essentially, in combination, at least one hydrocarbon oil and at least one aromatic ester oil. It will generally be desired that this carrier mixture is liquid (in the absence of structurant) at temperatures of 15° C. and above. It may have some volatility but its vapour pressure will often be less than 4 kPa (30 mmHg) at 25° C. so that the material can be referred to as a mixture of oils. More specifically, in most embodiments at least 50% by weight and in a number of embodiments at least 80% by weight of the hydrophobic carrier liquid consists of materials with a vapour pressure not over this value of 4 kPa at 25° C.

The hydrocarbon oils which can be incorporated in compositions herein include liquid aliphatic hydrocarbons such as mineral oils or hydrogenated polyisobutene, often selected to exhibit a low viscosity. Further examples of liquid hydrocarbons are polydecene and paraffins and isoparaffins of at least 10 carbon atoms and in many instances up to about 35 carbons. Many suitable liquid hydrocarbons contain from 12 to 25 carbons. Highly desirable results have been achieved employing a mineral oil and/or an isoparaffin. The hydrocarbon oil may be introduced at least in part as a carrier for one of the other constituents of the composition, such as the copolymer and/or may be introduced by itself.

In the essential liquid aromatic ester oils herein, the alkanol and acid residues or mixtures thereof are preferably selected such that the ester oils each have a melting point of below 20° C.

Suitable liquid aromatic esters for use in the compositions described herein can comprise esters derived from an aryl alcohol and an aryl acid, ie both moieties are aryl or esters in which one of the moieties is aryl and the other is alkyl, provided that they have a melting point that enables them to be a liquid at ambient temperature. Suitable esters include aryl benzoates of melting point at or below ambient temperature, for example benzyl benzoate. Preferred esters include fatty alkyl benzoate, alkyl or dialkyl naphthalate or fatty alkyl salicylate esters, and especially fatty alkyl benzoates. Examples of such esters include suitable $C_8$ to $C_{18}$ alkyl benzoates or mixtures thereof, including in particular $C_{12}$ to $C_{15}$ alkyl benzoates eg those available under the trademark Finsolv. Others include linear or branched $C_{10}$ to $C_{18}$ salicylate esters, eg butyloctyl salicylate. Such materials are commonly monoesters. They are particularly suitable for use herein. Yet others are dialkyl diesters eg $C_6$ to $C_{12}$ diesters of naphthalic acid, eg diethylhexyl-2,6-naphthalate.

Especially desired combinations of oils herein comprise a mixture of a mineral oil and/or an iso-paraffin oil with an alkyl benzoate (monoester), such as any of each described hereinabove.

The hydrocarbon and aromatic ester oils are employed herein in a weight ratio of 1:2 to 15:1, preferably in a weight ratio of at least 2:3 and particularly at least 1:1. In many suitable mixtures, the weight ratio is up to 10:1, in a number of desirable mixtures at up to 6:1 and especially at up to 4:1. Such weight ratios herein are based on the total weights of oils that are introduced, ie the total of oils that are introduced by themselves plus any amount from a premix or pre-dispersion, for example if or when it is acting as a carrier for some other constituent.

The total weight proportion of the carrier oils of the composition is usually selected in at least 45% and particularly at least 55%. In many embodiments, their total weight proportion is not more than 80% and in some preferred embodiments, is not more than 70%.

It is especially desirable in some embodiments to select a blend of carrier oils together with the antiperspirant active to achieve a near mis-match between the mean Refractive Index of the carrier oil blend and that of the antiperspirant active, for example within 0.06 and in many instances within 0.05 units, avoiding the need for close matching of the refractive indexes (RIs, eg to within 0.003 units). The difference in RI of the particulate antiperspirant and the carrier fluid in such embodiments is usually greater than 0.005 and commonly greater than 0.01 units. Such a respective near mis-match can be achieved readily by employing a aluminium chlorohydrate or activated aluminium chlorohydrate an antiperspirant active together with the entire range of blends of oils described above, or by employing an RI modified aluminium zirconium complex, the RI of which has been reduced to about 1.54 or lower, such as by a water treatment (hydration). The antiperspirant active is very preferably free from hollow particles, as indicated hereinbefore. The choice of a near mis-match rather than close matching renders the formulation more tolerant to small changes in the constituents and their proportions which can arise during manufacturing on a bulk scale.

Structurant System

Herein the structurant system employed comprises a combination of an organic wax and a di and/or tri block alkyl/aryl copolymer. The combined weight of the structurant system is usually at least 5.5%; in many preferred embodiments the structurant system is up to 12% by weight. In a number of desirable embodiments, at least 6% by weight of the structurant system is employed. In various particularly suitable embodiments not more than 9% by weight of the structurant system is employed. The weight ratio of the organic wax to the block copolymer is usually at least 6:1 and often is at least 8:1. In many suitable embodiments, its weight ratio is up to 24:1 and especially is up to 16:1. To some extent, it is desirable to vary the weight proportion of the copolymer inversely to that of the organic wax, for example selecting the weight proportions of both components of the system such that the numerical product obtained by multiplying the weight proportion of organic wax with the weight proportion of the copolymer falls in the range of from 4 to 6.5.

Organic Wax

This term "organic wax" is applied herein to a variety of organic materials including mixtures which have similar physical properties, namely that:— they are solid at 30° C. and preferably also at 40° C.;
they melt to a mobile liquid at a temperature above 30° C. but generally below 95° C. and preferably in a temperature range of 40° C. to 90° C.;
they are water-insoluble and remain water-immiscible when heated above their melting point.

Accordingly, the term organic wax comprises not only natural waxes, which traditionally were derived from plant material, possibly via concentration by bees, but also synthesised waxes and other organic materials that are waxy and thus resemble waxes.

Organic waxes are usually hydrocarbon waxes, waxy linear fatty alcohols, waxes comprising esters of fatty acids or mixtures containing such compounds along with a minority (less than 50%) of other compounds. Naturally occurring waxes are often mixtures of compounds which include a substantial proportion likely to be a majority of fatty esters. Organic waxes form crystals in the water-immiscible liquid when it cools from the heated state during processing.

These crystals take various forms including needles and platelets depending on the individual waxes. Some waxes form a network of fibrous crystals.

Examples of hydrocarbon waxes include paraffin wax, ozekerite, microcrystalline wax and polyethylene waxes with molecular weight of 2,000 to 10,000.

Examples of ester waxes include esters of long chain fatty acids with glycerol or ethylene glycol, such as $C_{18-36}$ fatty acids or $C_{16}$-$C_{22}$ fatty acids or individual fatty acids such as linear saturated $C_{18}$ or $C_{22}$ acids. Such esters may be made synthetically and various triglyceride waxes are extractable from plants, as indicated below.

Examples of natural waxes include beeswax, carnauba, candelilla, and spermeceti waxes that are of vegetable origin and mineral waxes from fossil remains other than petroleum. Montan wax, which is an example of a mineral wax, includes non-glyceride esters of carboxylic acids, hydrocarbons and other constituents.

Other organic waxes comprise linear fatty alcohols, normally monohydric and commonly fully saturated containing from 14 to 24 carbons, of which suitable examples include cetyl alcohol, stearyl alcohol, eicosonyl alcohol and behenyl alcohol or mixtures of any two or more thereof.

Organic waxes useful in the present invention will generally be those found to thicken water-immiscible oils such as mineral oil when dissolved therein (by heating and cooling) at a concentration of 5 to 15% by weight.

Herein, organic waxes employed herein commonly crystallise on cooling to form spherulitic needles or small platelets, which are distributed through and impart structure to the carrier liquid. Castor wax is an example of waxes that often crystallise as needles.

Preferably, the weight of organic waxes in the composition is at least 5%, particularly at least 6%. In many desirable embodiments, its weight is not greater than 12%, and particularly up to 8.5% or 9%.

Block Copolymers

Herein, the structurant system comprises a minor proportion in relation to the above-mentioned organic wax of thermodynamically incompatible copolymers, by which is meant that the polymer contains two opposite and apparently incompatible segments, such as in particular one hard relatively insoluble and one soft relatively soluble segment. This can be provided by incorporating into the copolymer both an aryl polymer block (A) to provide the hard/insoluble segment and a polyalkylene block segment (B) to provide a soft/soluble segment. Each block commonly comprises at least 50 or at least 100 monomeric units. Such copolymers tend to provide a three-dimensional network which extends through out the carrier liquid, through physical cross-links, possibly with the formation of relatively insoluble sub-microscopic particles of the particular block, otherwise called domains. The copolymers can be linear.

The aryl monomer polymerised to form one segment (A) commonly comprises styrene, though alternative monomers comprising two or more fused rings can be used too. The polyalkylene segment (B) can be derived from butadiene, isoprene, ethylene/butylene and ethylene/propylene. Di-block copolymers have the form A-B and triblock copolymers preferably have the form A-B-A. The di-block and tri-block copolymers can be employed separately or a mixture of both can be used.

The block copolymer can be introduced into the composition in the form of a pre-dispersion of the block copolymer in at least part of the carrier liquids. Herein the term dispersion or pre-dispersion indicates that the dispersed material is distributed throughout its carrier fluid, often in the form of discrete particulates but possibly at or approaching a molecular scale at or resembling a solution. This pre-dispersion can sometimes be obtained commercially in the form of a gel of the copolymer in a hydrocarbon oil. Such pre-formed gels, according to the manufacturers contain the range of from 1 to 20% by weight. The inventors have found it convenient to employ pre-formed gels which contain the copolymer itself in the region of 1.5 to 4% by weight.

Various preformed gels are available from Aiglon under their trademark Transgel, from Penreco under their trademark Versagel and from Collaborative Laboratories under their trademark Polysynlane Gel, in which the copolymer has gelled a hydrocarbon oil selected from a mineral oil, hydrogenated polyisobutene or isodecane. Alternatively, a dispersion of the copolymer in a carrier oil system can be obtained by introducing the copolymer itself, into at least the hydrocarbon oil component of the carrier oil system, particularly at elevated temperature, such as from 70 to 102° C. Styrene/alkylene block copolymers are commercially available under the trade mark Kraton, such as Kraton D and especially Kraton G, from Kraton Polymer Business.

The weight proportion of the block copolymer or mixture of block copolymers in the composition is commonly low, often being at least 0.4% and less than 2%. Preferably, the weight proportion of the copolymer is at least 0.5%. Often it is not necessary to employ more than 1.25% by weight of it.

One further way of identifying a suitable proportion of block copolymer to employ is by adjusting the amount of copolymer such that the viscosity of a dispersion of the polymer in the chosen amount of the carrier blend alone falls within a preferred range. Such a dispersion is obtained by forming a mixture of the copolymer and the carrier liquid or blend of liquids at an elevated temperature, eg 80 to 85° C. and thereafter permitting the resultant mixture to cool to the temperature at which its viscosity is measured. Desirably, the resultant dispersion has a viscosity, when measured at 25° C. by a viscometer, eg a RV20 Rotovisco™ viscometer from Haake employing an SV1 cup and bob system, of at least 0.5 Pa.s, preferably at least 1 Pa.s, desirably up to 75 Pa.s, more desirably up to 50 Pa.s and even more desirably up to 25 Pa.s, viscosities measured at an applied shear stress of 15 Pa.

To some extent, the preferred proportion of structurant system varies in line with the proportion of carrier oils in the composition. It is often desirable to employ a weight ratio of carrier oils to structurant system within the range of from 6:1 to 10:1, particularly at least 7:1 and/or up to 9:1.

Optional Ingredients

Optional ingredients in compositions of this invention can include deodorants, for example at a concentration of up to about 10% w/w. Suitable deodorant actives can comprise deoperfumes, and/or microbicides, including particularly bactericides, such as chlorinated aromatics, including biguanide derivatives, of which materials known as Triclosan (Irgasan DP300™), Tricloban™, and Chlorhexidine warrant specific mention. A yet another class comprises biguanide salts such as available under the trade mark Cosmosil™.

Other optional ingredients include wash-off agents, often present in an amount of up to 10% w/w to assist in the removal of the formulation from skin or clothing. Such wash-off agents are typically nonionic surfactants such as esters or ethers containing a $C_8$ to $C_{22}$ alkyl moiety and a hydrophilic moiety which can comprise a polyoxyalkylene group (POE or POP) and/or a polyol.

The composition herein can incorporate one or more cosmetic adjuncts conventionally envisaged for antiperspirant soft solids. Such cosmetic adjuncts can include skin benefit agents such as glycerol, allantoin or lipids, for example in an amount of up to 5%; and soluble colorants. Skin cooling agents such as menthol and menthol derivatives, often in an amount of up to 2%, all of these percentages being by weight of the composition. A commonly employed adjunct is a perfume, which is normally present at a concentration of from 0 to 4% and in many formulations from 0.25 to 2% by weight of the composition.

The formulations can also include, if desired, a small particle sized inorganic thickener, often in an amount of from 0.1 to 2% by weight. Finely particulate silica, eg fumed silica, such as available as Aerosil™ 200 represents a preferred inorganic thickener.

In addition to the two above-identified essential constituents of the liquid carrier, in some embodiments, a minor fraction of the liquid carrier can comprise one or more auxiliary oils such as hydrophobic carrier oils selected from silicone oils, be they volatile and/or non-volatile, polymeric aliphatic ethers, and aliphatic esters. Such auxiliary oils have a melting point of not higher than 25° C. commonly not above 20° C. and a boiling point of not below 100° C.

Suitable volatile silicone oils comprise linear methicones and preferably cyclomethicones, usually containing from 4 to 7 silicon atoms, such as in particular D5. Examples include those available from Dow Corning Inc under their marks DC245 or DC345. Suitable non-volatile silicone oils commonly comprise linear alkyl/aryl methicones such as that available from Dow Corning Inc under their mark DC556 or DC704 and linear methicones of higher viscosity than volatile silicones such as those within the range available from Dow Corning Inc under their trademark DC200 having a viscosity of at least 10 centipoise (Pa.s).

Suitable polymeric aliphatic ethers include those ethers having a polypropylene glycol moiety of from 10 to 20 units terminated by a $C_4$ to $C_6$ aliphatic alcohol such as butanol, eg the ether referred to as PPG-14 butyl ether in the CFTA Handbook.

Suitable aliphatic esters contain at least one long chain saturated hydrocarbon group, eg an alkyl group, such as esters derived from $C_1$ to $C_{20}$ alkanols, commonly monohydric alcohols, esterified with a $C_8$ to $C_{22}$ alkanoic acid. The saturated hydrocarbon can be embedded within a $C_6$ to $C_{10}$ alkanedioic acid or diol that is esterified by a respective alkyl $C_1$ to $C_{18}$ alkanol or carboxylic acid and especially a group containing $\geq 3$ carbons. These esters include isopropyl myristate, lauryl myristate, isopropyl palmitate, diisopropyl sebacate and diisopropyl adipate.

Suitable aliphatic esters commonly comprise at least one fatty moiety, such as an alkyl group of from 12 to 22 carbons linked via an ester linkage to a shorter chain length alkyl or alkylene moiety containing from 1 to 6 carbons. The aliphatic moieties can be linear or branched. Examples of triesters include triglycerides containing one $C_{12}$-$C_{25}$ alkyl substituent and two $C_1$-$C_4$ alkyl substituents.

The total proportion of such auxiliary oils is normally not greater than 15% by weight of the total weight of carrier oils, in many embodiments not greater than 10% and very desirably not greater than 5%.

The carrier liquid can include, if desired, a liquid moisturising agent, such as a polyhydric humectant, of which glycerol is preferred. The proportion of such moisturising agent, if present, is often at least 0.5%, commonly not more than 10%, and in many instances is from 1 to 6% by weight of the carrier. Alternatively, such humectant can be bound with the antiperspirant salt.

It will be recognised that the compositions described herein do not mention by name various ingredients that have been contemplated in cosmetic or antiperspirant compositions published in literature, including patent specifications and journal articles. It is preferred to avoid incorporating each or any of such ingredients, or at least incorporate less than the proportion of such a non-preferred ingredient given in such prior published compositions.

The compositions of the instant invention can be prepared by a convenient process in which the structurant system, ie the organic wax and the copolymer, is dissolved or dispersed in the carrier fluid at a temperature above the melting point of the organic wax, the particulate antiperspirant active material is introduced into the mixture of carrier oils and structurant system and resultant composition is cooled to below its normal setting temperature, thereby forming a soft solid which can be caused to flow by the application of gentle pressure. The antiperspirant active is often introduced at a temperature intermediate between that at which the structurant system is dispersed in the carrier oils and that at which the composition sets, such as at a temperature in the range of about $\frac{1}{3}^{rd}$ to $\frac{2}{3}^{rds}$ above the setting temperature, for example, at about 65° C. if the carrier oil/structurant mixture is formed at 80° C. and the composition sets at 50° C.

The product (composition filled into a dispenser) can be made by introducing the composition whilst it is still mobile into the storage chamber of the dispenser through a filling aperture and thereafter closing the filling aperture. The filling aperture may be positioned at the dispensing end, ie top, of the dispenser barrel, and thereafter closed by fitting a top cover which is perforated by a number of dispensing apertures, optionally sealable by a cap, or positioned at the end opposite the dispensing end, ie bottom, of the barrel, and thereafter closed by inserting a close fitting platform or piston into the barrel and mechanism to advance it towards the dispensing end.

The filling can be accomplished by a conventional pour technique in which the composition commonly is maintained at a temperature of about 5 to 10° C. above its normal setting temperature and gravity fed through a nozzle into the dispenser. Alternatively, filling can be effected by injection under pressure as described in WO01/76409, desirably at a temperature within −3° C. to +1° C. of the normal setting temperature of the composition.

The dispenser for applying the composition topically to the body, and particularly to underarm regions commonly comprises a storage chamber, often in the form of a tubular barrel having at one end a topwall, commonly domed, that is penetrated by at least one dispensing aperture or a pattern of apertures in fluid communication with the storage chamber and a means disposed remote from the topwall that imparts pressure to the contents of the storage chamber and thereby impel it through the dispensing aperture. Such means can comprise the chamber having at least one side or basewall that can be deformed inwardly thereby reducing the volume of the chamber, for example in the manner of a pouch or squeezable tube, eg as described in WO00/50314. In an alternative and more conventional dispenser for antiperspirant formulations, such means comprises a close-fitting platform or piston that is located within a tubular barrel at the bottom of the storage chamber. The platform can be impelled towards the topwall manually, such as digitally, ie by a finger inserted within the barrel through a base aperture, or by an advance mechanism in which the platform is mounted on a spindle, typically via co-operating screw threads and the spindle is rotated, either by an externally protruding base-mounted rotor wheel as in U.S. Pat. No. 5,000,356 or by a ratchet and pawl as in U.S. Pat. No. 5,839,622.

To a first approximation, and in the absence of pressure-reducing means, the propensity of a given soft solid formulation to synerese in a dispensing container having dispensing apertures of similar size in its top wall is inversely related the proportion of the top wall surface area that the apertures occupy. Advantageously, the resistance of the formulations according to the instant invention to synerese enables them to be employed in dispensing containers that have a comparatively small area of its topwall penetrated by the dispensing aperture or apertures, such as below 14% without needing special pressure reducing means to mitigate or prevent syneresis. The dispensing apertures normally comprise at least 3% of the top wall surface area. In a number of suitable dispensers, the aperture proportion is from 3 to 13% of the top wall surface area.

The dispensing apertures need not be confined to a central region and are can suitably be distributed across the entire span of the topwall. The apertures can suitably be round, oval or elongate, be it straight or serpentine. Elongate apertures preferably terminate in radiussed ends. A mixture of shapes can be employed. Whilst the shape, pattern and number of apertures is at the discretion of the producer, the apertures preferably have a minimum diameter of 1 mm and particularly at least 1.5 mm. The diameter of circular apertures and minor diameter of non-circular apertures is often not more than 5 mm. It is desirable to employ a symmetrical array of apertures. Suitable patterns include parallel, concentric and/or radial distributions of the apertures. In many instances the number of apertures will be selected in the range of from 3 to 24, and often from 3 to 12.

Additionally, it is possible for the invention formulations to be employed without disadvantage in dispensing containers that either contain a mechanism for pressure relief or the apertures of which comprise more than about 15% of the top wall surface area, such as from about 15% to about 80%, or a such-back pressure relief mechanism in which the platform within the container is linked to an advance rotor wheel or button via an intermediate axially pointing serrated cog that initially advances the platform towards the top wall and subsequently permits it to partially retract.

Having described the instant invention and selected or preferred embodiments thereof in general terms, specific embodiments thereof will now be described in greater detail by way of example only.

FORMULATION EXAMPLES 1 TO 15 AND COMPARISONS CP1 to CP12.

The following ingredients were employed in the below-mentioned Examples and Comparisons:—

| No | Product description | Trade name and grade | Producer |
|----|---------------------|----------------------|----------|
| 1  | volatile D5 silicone oil | DC245 | Dow Corning |
| 2  | non-volatile silicone oil | DC200 350cst | Dow Corning |
| 3  | Fumed silica | Aerosil 200 | Degussa |
| 4  | microcrystalline wax | Multiwax 180-M | Witco |
| 5  | $C_{18-36}$ acid triglyceride wax | Syncrowax HGLC | Croda |
| 6  | gel -Dimethicone elastomer in cyclomethicone | DC9040 | Dow Corning |
| 7  | Aluminium zirconium trichlorhydrex gly [AZAG] | Reach 908 | Reheis |
| 8  | Glyceryl tribehenate wax | Syncrowax HRC | Croda |
| 9  | non-volatile silicone oil | DC200 10cst | Dow Corning |
| 10 | dextrin palmitate | Rheopearl KL | Chiba Flour Milling |
| 11 | activated aluminium chlorohydrate [AACH] | Aloxicoll LR | Giulini |
| 12 | C12-15 alkylbenzoate oil | Finsolv TN | Finetex |

-continued

| No | Product description | Trade name and grade | Producer |
|----|---------------------|---------------------|----------|
| 13 | Castor wax | Castorwax MP80 | Caschem |
| 14 | $C^{18-36}$ acid glycol ester wax | Syncrowax ERLC | Croda |
| 15 | gel - dimethicone/copolyol elastomer in mineral oil | KSG 31 | Shin-etsu |
| 16 | gel - block copolymer in hydrocarbon oil | Transgel 110 | Aiglon |
| 17 | Isoparaffin oil | Isopar M | Exxon Chemicals |
| 18 | Isoparaffin oil | Permethyl 101A | Presperse |
| 19 | Mineral oil | Sirius M70 | Fuchs |
| 20 | Mineral oil | Sirius M40 | Fuchs |
| 21 | gel - block copolymer in hydrocarbon oil | Versagel MD750 | Penreco |
| 22 | gel - block copolymer in hydrocarbon oil | Versagel ME750 | Penreco |
| 23 | gel - block copolymer in hydrocarbon oil | Versagel M750 | Penreco |
| 24 | gel - block copolymer in hydrocarbon oil | Polysynlane Gel | Collaborative Laboratories |
| 25 | Decyl Oleate oil | Cetiol V | Cognis |
| 26 | Octyl dodecanol oil | Eutanol G | Cognis |
| 27 | Diethylhexyl-2,6-naphthalate oil | HallBrite TQ | CP Hall |
| 28 | Butyloctyl Salicylate oil | HallBrite BHB | CP-Hall |
| 29 | Glycerol | Glycerol | Sigma Aldrich |

The Example and Comparison formulations were made by the following general method in which:—

1. The waxes and carrier oils were added together in the weight proportions indicated in the respective Table 1 or 2 below, stirred gently and heated until 90-95° C. is reached and the waxes have dissolved.
2. The block copolymer or elastomer was added and physically stirred in to ensure a uniform temperature throughout the mixture. Heating and mixing was continued at 90-95° C. until a homogeneous mixture was obtained.
3. Particulate antiperspirant active (ambient temperature) were then added under low shear (1500-2500 rpm) to ensure homogenous mixing without external heating.
4. The resultant fluid mixture was then poured into samples of the dispensing container/pack described below and allowed to cool to form a soft solid.

Dispensing Container

Figure 1:
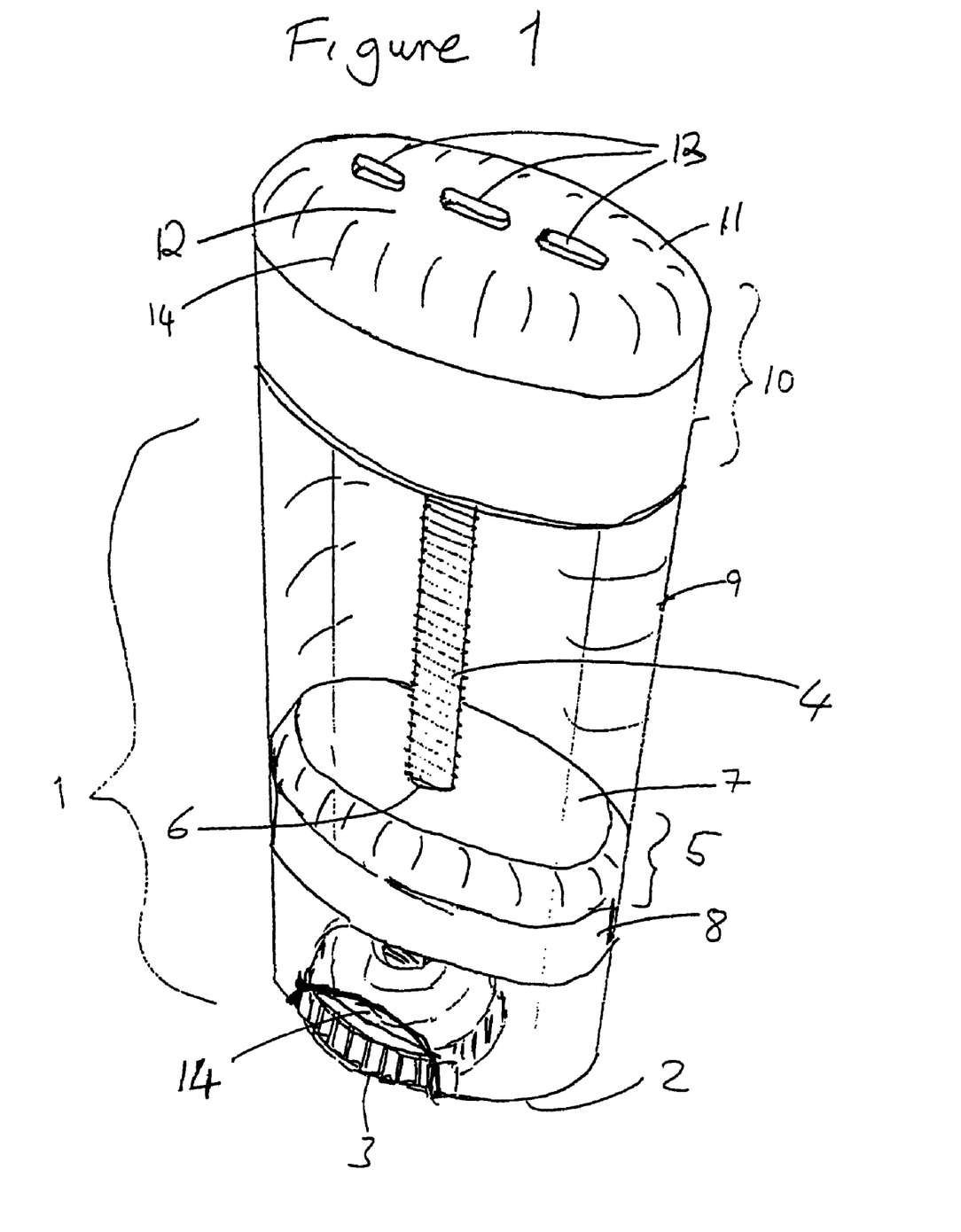

The dispensing container into which the Example and Comparison formulations were introduced is described herein with reference to FIG. 1 which provides a perspective view.

The container comprises a tubular container [1] of oval transverse cross section for the formulation made from translucent plastic having a base [2] provided with a central aperture acting as a housing an axially mounted thumbwheel [3] which is fixed to an axially extending screw threaded spindle [4]. Thumbwheel [3] is exposed through base sidewall opening [14]. A platform [5] mounted within the container [1] has a central internally screw threaded axial aperture [6] that engages with spindle [4] a domed upper top wall [7] and a dependent skirt [8] that fits in fluid-tight contact with the interior surface of the sidewall [9] the container [1]. The container [1] is closed at the end opposite the base [2] by a closure [10] having a domed top wall [11] or respective major and minor diameters of 5.6 mm and 31.5 mm having a central flattened area [12] which defines three elongate apertures [13] having lateral sides extending in parallel with the major transverse axis of the closure [10] terminating in radiussed ends and an outer area of radius 28 mm. The three apertures together constitute 3.6% of the surface area of dome [11], taking into account the curved nature of the dome.

Product Characterisation

Syneresis Score

The Syneresis Score was determined by visually inspecting filled dispensers that had been subjected to the test method described below. The method was carried out at laboratory ambient temperature, i.e. in the region of 22 to 23° C. during the laboratory working day, and falling to between 15 and 20° C. overnight.

Samples of dispensing containers according to FIG. 1 which had been filled and allowed to cool to ambient in the general preparative method described above were stored for 2 days or until the first working day thereafter and then subjected to one or more cycles of steps a) and b).

In each cycle, in step a) the platform in the dispenser was advanced towards the closure sufficiently to allow approximately 1 cm length of extrudate to extrude out through each of the three apertures in the dome of the closure. The extrudate was wiped off the dome using a paper towel. Step a) was carried out four times.

After the $4^{th}$ time that step a) had been completed, step b) was carried out, in which the dispenser was stored upright underneath a translucent beaker (to prevent contamination by foreign bodies) on the laboratory bench until the next working day. The domed closure was then examined visually to determine whether there had been any solvent leakage or other observable changes to the pack exterior/interior. Any sign of formulation leakage or other significant change was recorded. Any leakage was wiped off the dispenser using a paper towel.

The cycle of steps a) and b) was repeated for up to a further 5 cycles, i.e. up to a maximum of 6 cycles, each cycle comprising, extrusion and wiping off of formulation four times, storage of the dispenser until the next working day at laboratory ambient temperature and then a visual check and removal of surface material.

Each formulation was classified according to its ability to resist leakage as measured by the method described above. The results are summarised in the Tables below NnC—no syneresis observed after n cycles—ie a pass SnC—syneresis observed after n cycles—ie a failure Antiperspirant Efficacy Certain of the Example and comparison formulations were subsequently tested for their antiperspirant efficacy (sweat reduction) under a standard efficacy test protocol and compared with the efficacy achieved under the same hot room test conditions with a reference soft solid formulation of acceptable efficacy, viz. CP1. The protocol employs a panel of subjects to whom a reference sample is applied to one armpit and a test sample to the other, with a left/right balance for the two samples. The test enables the relative sweat reduction of the test compared with the reference formulation to be determined Fail indicated that the sweat reduction achieved was markedly lower than that achieved by application of the reference soft solid CP1, being in the region of ⅔rds or lower. This was considered to be unacceptable. Pass indicated that the sweat reduction achieved was similar to that from the reference soft solid, ie above ⅚ths and was considered to be acceptable.

A blank in subsequent Tables 1 and 2 indicates either the absence of that ingredient or that the particular characterisation has not been carried out.

Viscosity Measurement

For some of the Examples, the viscosity of a dispersion of the block copolymer in the carrier oils in their respective weight ratios was measured at 25° C. on a Haake RV20 Rotovisco viscometer using a SV1 cup and bob system, at a constant shear stress of 15 Pa.S. This is shown in Table 2 as Polymer Viscosity Comparisons CP1 to CP12

TABLE 1

| Ingredients | Comparison No | | | | | |
|---|---|---|---|---|---|---|
| | CP1 | CP2 | CP3 | CP4 | CP5 | CP6 |
| | % by weight | | | | | |
| Cyclomethicone (1) | 55 | 62.75 | | | | 26.8 |
| Dimethicone 350cst (2) | 8 | | | | | |
| Silica (3) | 1 | | | 1.5 | | |
| MicroXtalline wax (4) | 3.25 | | | | | |
| Triglyceride wax (5) | 3.25 | 1.25 | | | | |
| Elastomer gel (6) | 4 | | | | | |
| AZAG (7) | 25.5 | 26 | | | | |
| Glyceride wax (8) | | 5 | | | | |
| Dimethicone 10cst (9) | | 5 | | | | |
| Dextrin palmitate (10) | | | 10 | | 3 | |
| AACH (11) | | | 25.5 | 25.5 | 25.5 | 25.5 |
| Benzoate oil (12) | | | 64.5 | 63 | 31.5 | |
| castor wax (13) | | | 7.5 | | 5.625 | |
| glycol ester wax (14) | | | 2.5 | | 1.875 | |
| Elastomer gel (15) | | | | 40 | | |
| Transgel 110 (16) | | | | | 40.2 | |

| | Characterisation | | | | | |
|---|---|---|---|---|---|---|
| Syneresis Score* | S1C | S1C | S1C | S1C | N6C | S2C |
| Efficacy | Ref | | | pass | fail | |

| Ingredients | Comparison No | | | | | |
|---|---|---|---|---|---|---|
| | CP7 | CP8 | CP9 | CP10 | CP11 | CP12 |
| | % by weight | | | | | |
| Cyclomethicone (1) | 18.4 | | | | | |
| AZAG (7) | | | 25.5 | 25.5 | 25.5 | 25.5 |
| AACH (11) | 25.5 | 25.5 | | | | |
| Decyl oleate (25) | | | | | | 36.5 |
| Octyl dodecanol (26) | | | | | 36.5 | |
| Isoparaffin (18) | | | | 36.5 | | |
| Mineral oil (19) | | | 36.8 | | | |
| Benzoate oil (12) | 18.4 | 44.7 | | | | |
| Castor wax (13) | 5.625 | | 5.625 | 5.625 | 5.625 | 5.625 |
| glycol ester wax (14) | 1.875 | | 1.875 | 1.875 | 1.875 | 1.875 |
| Transgel 110 (16) | 30.2 | 29.8 | 30.2 | 30.2 | 30.2 | 30.2 |

| | Characterisation | | | | | |
|---|---|---|---|---|---|---|
| Syneresis Score* | S6C | S1C | S5C | S4C | S1C | S1C |

Comparison formulation CP1 was a reference soft solid formulation similar to a formulation that was commercially available in 2001. Formulations in comparisons CP1 to CP4 comprised various carrier fluids and wax structurants, comparisons CP3 and CP4 employing a member of a class of carrier fluids employed in the instant invention. They all had or were expected to have acceptable efficacy, but demonstrated a very low resistance to syneresis, because syneresis was observed after the first cycle from a dispenser which did not contain a pressure relief mechanism but which used a domed closure in which the apertures represented below 5% of its surface area.

CP5 employed a different structurant system but a carrier fluid system comprising an ester oil and a mineral oil that is in accordance with the present invention. Although it demonstrated good resistance to syneresis, it failed to provide acceptable efficacy.

Examples CP6 to CP12 all contained a block copolymer, employing a range of solvent systems and combinations with wax structurants. All failed the syneresis test.

CP6 contained waxes and a volatile silicone. CP7 contained an aromatic ester as well as a significant proportion of volatile silicone. CP8 did not contain a wax. It was very sticky and poured from the dispenser. CP9 to CP12 contained an additional carrier other than an aromatic ester.

This shows that the presence of the block copolymer as a structurant is not sufficient by itself to ensure non-syneresis, even when employed in a selected carrier oil system or in combination with a wax.

Examples 1-15

TABLE 2

| Ingredients | Example No | | | | | |
|---|---|---|---|---|---|---|
| | 1 | 2 | 3 | 4 | 5 | 6 |
| | % by weight | | | | | |
| Transgel 110 (16) | 40.2 | 30.2 | 40.2 | 30.2 | 30.2 | 30.2 |
| Benzoate oil (12) | 26.8 | 18.4 | 26.8 | 18.4 | 18.4 | 18.4 |
| Isoparaffin (17) | | 18.4 | | | | |
| Isoparaffin (18) | | | | 18.4 | | |
| Mineral oil (19) | | | | | 18.4 | |
| Mineral oil (20) | | | | | | 18.4 |
| Castor wax (13) | 5.625 | 5.625 | 5.625 | 5.625 | 5.625 | 5.625 |
| glycol ester wax (14) | 1.875 | 1.875 | 1.875 | 1.875 | 1.875 | 1.875 |
| AACH (11) | 25.5 | 25.5 | | | | |
| AZAG(7) | | | 25.5 | 25.5 | 25.5 | 25.5 |

| | Characterisation | | | | | |
|---|---|---|---|---|---|---|
| Syneresis Score | N6C | N6C | N6C | N6C | N6C | N6C |
| Efficacy | pass | pass | pass | | | |
| Polymer Viscosity Pa · s | 49.2 | 3.3 | 2.9 | 3.9 | 2.9 | |

| Ingredients | Example No | | | | | |
|---|---|---|---|---|---|---|
| | 7 | 8 | 9 | 10 | 11 | 12 |
| | % by weight | | | | | |
| Transgel 110 (16) | | | | | | 35.2 |
| Versagel MD750 (21) | | | | 40.2 | 35.2 | |

TABLE 2-continued

| | | | | | | |
|---|---|---|---|---|---|---|
| Versagel ME750 (22) | | 40.2 | | | | |
| Versagel M750 (23) | | | 40.2 | | | |
| Polysynlane Gel (24) | 40.2 | | | | | |
| Benzoate oil (12) | 21.4 | 26.8 | 26.8 | 26.8 | 15.9 | 27.3 |
| Isoparaffin (17) | | | | | 15.9 | |
| Castor wax (13) | 5.625 | 5.625 | 5.625 | 5.625 | 5.625 | 9 |
| glycol ester wax (14) | 1.875 | 1.875 | 1.875 | 1.875 | 1.875 | 3 |
| AACH (11) | 25.5 | | | 25.5 | | 25.5 |
| AZAG (7) | | 25.5 | 25.5 | | 25.5 | |

| Characterisation | | | | | | |
|---|---|---|---|---|---|---|
| Syneresis Score | N6C | N6C | N6C | N6C | N6C | N6C |
| Efficacy | | | | pass | | |
| Polymer Viscosity Pa · s | 24.4 | 14.8 | 10.1 | — | — | — |

| | Example No | | |
|---|---|---|---|
| | 13 | 14 | 15 |
| Ingredients | % by weight | | |
| Transgel 110 (16) | 40.4 | 27.5 | 40.2 |
| Benzoate oil (12) | 22.0 | 27.5 | 24.8 |
| Naphthalate oil (27) | 5.0 | | |
| Salicylate oil (28) | | 10 | |
| Glycerol | | | 2.0 |
| Castor wax (13) | 5.7 | 7.5 | 5.625 |
| glycol ester wax (14) | 1.9 | 2.5 | 1.875 |
| AACH (11) | 25.0 | 25.5 | 25.5 |

| Characterisation | | | |
|---|---|---|---|
| Syneresis Score | N6C | N6C | N6C |

All Examples 1 to 15 demonstrated improved and acceptable resistance to syneresis compared with related comparison formulations CP6 to CP12. The Example formulations also had acceptable efficacy, that wass similar to reference soft solid CP1, as demonstrated by the results obtained for representative Examples 1, 2, 3 and 10. The efficacy of such Example formulations was markedly superior to the efficacy of Comparison formulation CP5 employing the same classes of carrier oils.

What we claim is:

1. A cosmetic composition in the form of an anhydrous soft solid, said cosmetic composition comprising at least 60% by weight in total of a water immiscible carrier liquid and structurant system therefor, and from 1 to 30% by weight of a particulate antiperspirant active suspended in said carrier liquid said carrier liquid comprising a mixture of a hydrocarbon oil and an aromatic ester oil in a weight ratio of from 1:2 to 15:1 and said structurant system comprising a di or triblock alkylene/arylene block copolymer and an organic wax in a weight ratio to each other of from 5:1 to 1:30, and wherein the carrier liquid optionally further comprises an auxiliary hydrophobic carrier oil, wherein the total amount of the auxiliary hydrophobic carrier oil, if present, is not greater than 15% by weight of the total weight of the carrier liquid, and wherein the structurant system comprises from 5.5% to 20% by weight of the composition, and wherein the total weight proportion of carrier oils in the composition is at least 45% and is not more than 80%.

2. A cosmetic composition according to claim 1 wherein the weight ratio of hydrocarbon oil to aromatic ester oil is at least 2:3.

3. A cosmetic composition according to claim 2 wherein the weight ratio of hydrocarbon oil to aromatic ester oil is at least 1:1.

4. A cosmetic composition according to claim 1 wherein the weight ratio of hydrocarbon oil to aromatic ester oil is up to 6:1.

5. A cosmetic composition according to claim 4 wherein the weight ratio of hydrocarbon oil to aromatic ester oil is up to 4:1.

6. A cosmetic composition according to claim 1 wherein the weight ratio of hydrocarbon oil to aromatic ester oil is from 1:1 to 4:1.

7. A cosmetic composition in the form of an anhydrous soft solid, said cosmetic composition comprising at least 60% by weight in total of a water immiscible carrier liquid and structurant system therefor, and from 1 to 30% by weight of a particulate antiperspirant active suspended in said carrier liquid said carrier liquid comprising a mixture of a hydrocarbon oil and an aromatic ester oil in a weight ratio of from 1:1 to 4:1 and said structurant system comprising a di or triblock alkylene/arylene block copolymer and an organic wax in a weight ratio to each other of from 5:1 to 1:30, and wherein the carrier liquid optionally further comprises an auxiliary hydrophobic carrier oil, wherein the total amount of the auxiliary hydrophobic carrier oil, if present, is not greater than 15% by weight of the total weight of the carrier liquid and wherein the total weight proportion of carrier oils in the composition is from 55 to 70%, and wherein the structurant system comprises from 5.5% to 20% weight of the composition.

8. A cosmetic composition according to claim 1 wherein the total weight proportion of carrier oils in the composition is not more than 70%.

9. A cosmetic composition according to claim 1 wherein the total weight proportion of carrier oils in the composition is from 55 to 70%.

10. A cosmetic composition according to claim 1 wherein the weight ratio of carrier oils to structurant system is within the range of from 6:1 to 10:1.

11. A cosmetic composition according to claim 10 wherein the total weight proportion of carrier oils in the composition is from 55 to 70%.

12. A cosmetic composition according to claim 10 wherein the weight ratio of hydrocarbon oil to aromatic ester oil is from 1:1 to 1:4.

13. A cosmetic composition according to claim 1 wherein the structurant system comprises at least 6% by weight of the composition.

14. A cosmetic composition according to claim 1 wherein the structurant system comprises not more than 12% by weight of the composition.

15. A cosmetic composition according to claim 10 wherein the structurant system comprises from 6% to 12% by weight of the composition, the weight ratio of carrier oils to structurant system is within the range of from 6:1 to 10:1 and the weight ratio of hydrocarbon oil to aromatic ester oil in the carrier oils is from 1:1 to 4:1.

16. A cosmetic composition according to claim 1 wherein the weight ratio or the organic wax to the block copolymer is at least 8:1.

17. A cosmetic composition according to claim 1 wherein the weight ratio or the organic wax to the block copolymer is up to 24:1.

18. A cosmetic composition according to claim 1 wherein the numerical product obtained by multiplying the weight percentage of organic wax with the weight percentage of the block copolymer is in the range of 4 to 6.5.

19. A cosmetic composition according to claim 1 wherein the weight percentage of organic wax in the composition is from 6 to 9%.

20. A cosmetic composition according to claim 1 wherein the organic wax comprises one or more waxes selected from hydrocarbon waxes, waxy linear fatty alcohols and esters of fatty acids or mixtures thereof said wax being solid at 40° C.

21. A cosmetic composition according to claim 20 wherein the wax comprises ester derived from fatty acids and glycerol and/or ethylene glycol.

22. A cosmetic composition according to claim 1 wherein the arylene/alkylene block copolymer is derived from styrene and butadiene or isoprene or ethylene/butylene or ethylene propylene.

23. A cosmetic composition according to claim 1 wherein the block copolymer is introduced into the composition in the form of a pre-dispersion in a hydrocarbon oil.

24. A cosmetic composition according to claim 23 wherein the concentration of the block copolymer in the pre-dispersion is from 1.5 to 4% by weight.

25. A cosmetic composition according to claim 1 wherein a dispersion of the block copolymer in the carrier oils has a viscosity of from 1 to 25 Pa·s when measured at 25° C. in a viscometer.

26. A cosmetic composition according to claim 15 wherein the structurant comprises from 6 to 9% of said organic wax is selected from the group consisting of hydrocarbon waxes, waxy linear fatty alcohols and esters of fatty acids and mixtures thereof that are solid at 40° C. and said arylene/alkylene block copolymer is derived from styrene and butadiene or isoprene or ethylene/butylene or ethylene propylene.

27. A cosmetic composition according to claim 1 wherein the antiperspirant active is an astringent aluminium and/or zirconium salt preferably a halohydrate.

28. A cosmetic composition according to claim 27 wherein the astringent salt is an aluminium and/or zirconium chlorohydrate, optionally activated, and/or an aluminium/zirconium complex with an amino acid.

29. A cosmetic composition according to claim 28 wherein the astringent salt is an activated aluminium chlorohydrate or an aluminium zirconium chlorohydrate complexed with glycine.

30. A cosmetic composition according to claim 27 wherein the antiperspirant active is free from hollow particles and has a refractive index which differs from the average refractive index of the carrier liquids by from 0.01 to 0.05 units.

31. A cosmetic composition according to claim 30 wherein the weight ratio of hydrocarbon oil to aromatic ester oil is from 1:1 to 4:1 and the total weight proportion of carrier oils in the composition is from 55 to 70%.

32. A cosmetic composition according to claim 31 wherein the weight ratio of carrier oils to structurant system is within the range of from 6:1 to 10:1.

33. A cosmetic composition according to claim 31 wherein the structurant comprises from 6 to 9% of said organic wax is selected from the group consisting of hydrocarbon waxes, waxy linear fatty alcohols and esters of fatty acids and mixtures thereof that are solid at 40° C. and said arylene/alkylene block copolymer is derived from styrene and butadiene or isoprene or ethylene/butylene or ethylene propylene.

34. A cosmetic method of controlling perspiration comprising applying topically to skin a cosmetic composition according to claim 1.

* * * * *